Figure 1:
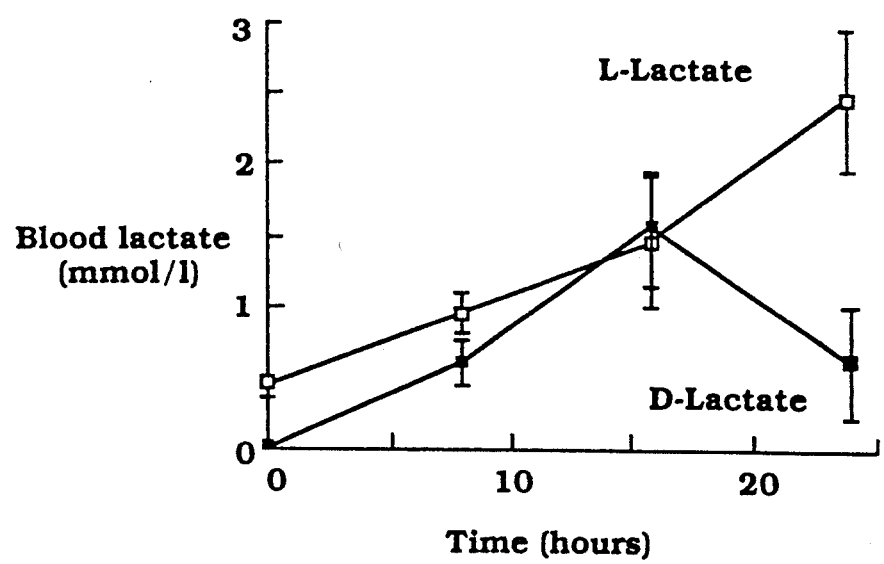

United States Patent [19]

Rowe

[11] Patent Number: 5,204,361
[45] Date of Patent: Apr. 20, 1993

[54] METHOD FOR TREATING LAMINITIS IN EQUINE LIVESTOCK

[76] Inventor: James B. Rowe, Lot 14 Amherst Ave., Darlington, Western Australia 6070, Australia

[21] Appl. No.: 331,581

[22] Filed: Mar. 30, 1989

[30] Foreign Application Priority Data

Mar. 30, 1988 [AU] Australia ................. PI7526
Nov. 1, 1988 [AU] Australia ................. PJ1239
Jan. 9, 1989 [AU] Australia ................. PJ2218

[51] Int. Cl.$^5$ .................. A61K 31/42; A61K 37/00
[52] U.S. Cl. ........................ 514/375; 514/9; 514/11
[58] Field of Search ................... 514/375, 9, 11

[56] References Cited

U.S. PATENT DOCUMENTS

| | | | |
|---|---|---|---|
| 3,017,272 | 1/1962 | Van Dijck et al. | 424/121 |
| 4,218,437 | 8/1980 | Hiller | 424/94.2 |
| 4,235,879 | 11/1980 | Hiller | 424/94.66 |
| 4,336,250 | 6/1982 | Scheifinger | 514/9 |
| 4,859,690 | 8/1989 | Lam et al. | 514/375 |

OTHER PUBLICATIONS

The Merck Veterinary Manual, Fifth Ed (1979), Merck & Co., Inc., Rahway, N.J., p. 493.
Rowe, James Baber, Prior Art with Respect to the U.S. patent application "Treatment of Equine Livestock" (1977), U.S. Ser. No. 07/331,581.

Primary Examiner—Frederick E. Waddell
Assistant Examiner—Kevin F. Weddington
Attorney, Agent, or Firm—Harness, Dickey & Pierce

[57] ABSTRACT

A method of treating or preventing laminitis in equine livestock which comprises delivering to the lower alimentary canal a quantity of an agent comprising virginiamycin, virginiamycin M or virginiamycin S.

15 Claims, 6 Drawing Sheets

METHOD FOR TREATING LAMINITIS IN EQUINE LIVESTOCK

This invention relates to the treatment of equine livestock such as horses, donkeys, ponies, mules and like livestock.

In one form the invention resides in an agent for the treatment of equine livestock comprising a glycopeptide antibiotic or a glycolipid antibiotic or a staphylomycin antibiotic or a polypeptide antibiotic or a macrolide antibiotic or a sulphur-containing peptide antibiotic or a lincosamide antibiotic, or tiamulin or a nitrofuran antibiotic or a tetracycline antibiotic or a penicillin antibiotic or a polythiazole antibiotic or ionophore antibiotic or any other antibiotic which are active against gram-positive bacteria or any combination thereof.

According to a preferred feature of the invention the agent is for the treatment of laminitis in equine livestock by controlling lactic acid concentration in the hind gut.

According to a preferred feature of the invention the agent is for improving the efficiency of feed utilization in equine livestock by increasing the production of propionate during fermentative digestion in the hind gut.

According to a preferred feature of the invention the agent is presented in a particulate form which is able to withstand the enzymatic digestion of the upper alimentary canal and enhances its uptake into the caecum.

According to a preferred feature of the previous feature the particle size is as least approximately 1 mm in size.

According to a preferred feature of the previous feature the particles are of a fibrous nature. According to a preferred feature of the invention the glycopeptide antibiotic comprises avoparcin.

According to a preferred feature of the invention the glycopeptide antibiotic comprises vancomycin.

According to a preferred feature of the invention the glycolipid antibiotic comprises flavomycin (bambermycin).

According to a preferred feature of the invention staphylomycin antibiotic comprises virginiamycin.

According to a preferred option of the invention the polypeptide antibiotic comprises bacitracin zinc.

According to a preferred option of the invention the polypeptide antibiotic comprises bacitracin methylene disalicylate.

According to a preferred option of the invention the polypeptide antibiotic comprises virginiamycin A.

According to a preferred option of the invention the polypeptide antibiotic comprises polymixins (B & E).

According to a preferred feature of the invention the macrolide antibiotic comprises tylosin.

According to a preferred feature of the invention the macrolide antibiotic comprises spiramycin.

According to a preferred feature of the invention the macrolide antibiotic comprises virginiamycin M.

According to a preferred feature of the invention the macrolide antibiotic comprises josamycin.

According to a preferred feature of the invention the macrolide antibiotic comprises spectinomycin.

According to a preferred feature of the invention the macrolide antibiotic comprises erythromycin.

According to a preferred feature of the invention the sulphur-containing peptide antibiotic comprises thiopeptone.

According to a preferred feature of the invention the sulphur-containing peptide antibiotic comprises sulfomycin.

According to a preferred feature of the invention the sulphur-containing peptide antibiotic comprises thiostrepton.

According to a preferred feature of the invention the sulphur-containing peptide antibiotic comprises sporangiomycin.

According to a preferred feature of the invention the sulphur-containing peptide antibiotic comprises siomycin.

According to a preferred feature of the invention the sulphur-containing peptide antibiotic comprises taitomycin.

According to a preferred feature of the invention the lincosamide antibiotic comprises lincomycin.

According to a preferred feature of the invention the lincosamide antibiotic comprises clindamycin.

According to a preferred feature of the invention the agent comprises tiamulin.

According to a preferred feature of the invention the nitrofuran antibiotic comprises nitrofurantoin.

According to a preferred feature of the invention the nitrofuran antibiotic comprises nitrofurazone.

According to a preferred feature of the invention the nitrofuran antibiotic comprises furazolidone.

According to a preferred feature of the invention the tetracycline antibiotic comprises chlortetracycline.

According to a preferred feature of the invention the tetracycline antibiotic comprises oxytetracycline.

According to a preferred feature of the invention the polythiazole antibiotic comprises nosiheptide.

According to a preferred feature of the invention the antibiotic comprises novobiocin sodium.

According to a preferred feature of the invention the antibiotic comprises bottromycin tartrate.

According to a preferred feature of the invention the antibiotic comprises streptogramin.

According to a preferred feature of the invention the antibiotic comprises nitrovin (payzone).

According to a preferred feature of the invention the antibiotic comprises enramycin.

According to a preferred feature of the invention the penicillin antibiotic comprises penicillin V.

According to a preferred feature of the invention the ionophore antibiotic comprises lasalocid.

According to a preferred feature of the invention the ionophore antibiotic comprises tetronasin.

According to a preferred feature of the invention the ionophore antibiotic comprises naracin.

According to a preferred feature of the invention the ionophore antibiotic comprises salinomycin.

According to a preferred feature of the invention the penicillin antibiotic comprises ampicillin.

In another form the invention resides in a method of treating equine livestock which comprises delivering to the lower alimentary canal a quantity of an agent of the form described above.

According to a preferred feature of the invention the method is for treating equine livestock which are the subject of a high carbohydrate diet by controlling lactic acid concentration in the hind gut to prevent laminitis.

According to a preferred feature of the invention the agent is administered regularly throughout the period the animal is subjected to a high carbohydrate diet.

According to a preferred feature of the invention the agent is administered in a single dose subsequent to the consumption of an excessive quantity of high carbohydrate food stuff.

According to a preferred feature of the invention the method is for treating equine livestock to increase the production of proprionate during fermentation digestion in the hind gut.

According to a preferred feature of the invention the agent is administered orally.

The digestive processes in the horse include gastric digestion where enzymes act on the ingested feed in an acid stomach followed by absorption of nutrients from the small intestine and then fermentative digestion in the caecum, colon and large intestine. The volume of the caecum, colon and large intestine can be around 50 to 60 liters and on most diets the end products of fermentation in these parts of the tract provide more than half of the energy available to the animal. The principal end products of fermentation are three volatile fatty acids: acetic acid; propionic acid; and butyric acid. A description of the pathways by which these acids are produced is required in order to understand how modification of their relative importance as end products of fermentation can enhance equine performance.

During microbial fermentation, carbohydrates including cellulose, hemicellulose, starch and sugars are first broken down to 6-carbon compounds (hexose). These are then fermented through pyruvate to the volatile fatty acids. From 1 mole of hexose it is possible to obtain 2 moles of acetic acid, or two moles of propionic acid or one mole of butyric acid. When acetic acid is the end product, 2 moles contain 1.75 MJ of energy compared to 3.08 MJ contained in 2 moles of propionic acid and 2.20 MJ contained in one mole of butyric acid. Therefore when the production of propionic acid increase relative to that of acetic and butyric acids, there is more energy available to the animal per unit of carbohydrate fermented.

The volatile fatty acids are utilized by the animal through different biochemical pathways in the liver and the body tissues. Acetic and butyric acids cannot be used for the synthesis of glucose. On the other hand, propionic acid is converted by the liver to glucose. Glucose is an essential nutrient for many of the body tissues such as the brain and the kidneys and is also the basic component of glycogen which is the principal store of biochemical energy in the muscle. Glycogen is rapidly broken down to glucose for use by muscle when animals are exercising and its availability may influence the performance of an animal where speed and/or endurance are being tested. Increased propionic acid production in the caecum and colon may therefore enhance the deposition of glycogen.

When acetic or butyric acids are produced during fermentation the gas, carbon dioxide, is also produced. Part of this carbon dioxide is converted to the gas methane. Some of these said gasses are absorbed from the gastrointestinal tract and some are expelled as flatus. Under some conditions the gas is produced more rapidly than it is removed and the build-up of gas results in distension of the bowel which causes severe pain (colic) to the animal. A pattern of fermentation where propionic acid production is increased results in less gas being produced and thereby decreases the amount of gas expelled as flatus and also decreases the likelihood of gas accumulation causing colic.

When horses consume grain, or any other feed which contains starch or soluble carbohydrate, part of this is digested by fermentation in the caecum and colon. Starch and soluble carbohydrate provide a substrate for bacteria which is rapidly fermented. The direct results of this rapid fermentation include the following changes: increased rate of volatile fatty acid production; decreased pH; increased molar proportion of propionic acid relative to acetic acid and butyric acid; and the accumulation of lactic acid. It is known that associated with the feeding of high levels of starch or soluble carbohydrate to horses are a number of adverse effects on the animal. These (carbohydrate overload) effects on the animal include: adverse behaviour (more time eating wood, and coprophagia); increased testosterone levels; lowered blood pH; decreased blood bicarbonate concentration; a deficit in blood bases; increased body temperature; increased blood lactic concentration and laminitis which can lead to lameness. Laminitis, or founder, is an inflammation of the horses foot. Laminae are located between the bone and the hoof and contain the blood vessels "servicing" the hoof. When inflamed the laminae between these two rigid surfaces swell, causing pressure, pain and tissue damage. Through anteriovenous shunts blood supply to the inflamed tissue is cut off and this results in ischaemic necrosis of the laminae at the front of the hoof. In severe cases the hoof may separate from the underlying laminae or downward rotation of the "coffin" bone in the foot may occur. The biological pathway linking carbohydrate overload with laminitis is not known but there is clear evidence that when high levels of grain or lush green grass are fed laminitis and lameness can result. It has been found that these adverse effects are closely correlated with low pH, and high lactic acid in the caecum and colon. Therefore it is preferred that control of low pH and high levels of lactic acid in the caecum and colon would therefore reduce or remove the adverse effects on the animal when starch or soluble carbohydrate are fed as a major component of the diet.

Current nutritional management of equine animals requires that approximately half of the diet is roughage and that only limited amounts of starch are fed. This feeding regime is designed to avoid laminitis which is well known to be associated with too much starch in the diet. If it were possible to feed additional grain (starch) and less roughage, there would be a number of advantages. These are listed below:

(i) Reduce the amount of digesta in the hind gut of the horse and thereby reduce the total body weight of the animal without affecting the muscle mass.

(ii) Facilitate the practice of "carbohydrate loading" used in the nutritional management of athletes. This practice requires the feeding of starch and soluble carbohydrate prior to racing or performance in order to boost muscle glycogen reserves.

(iii) Reduce the cost of feeding horses. Starch-rich grains are cheaper sources of digestible energy than the high quality roughages (hay and chaff) normally required for horse feeding.

Lactic acid in the blood and tissues of horses can originate from two sources. (i) It can be formed when glucose is used as an energy source by muscle in the presence of insufficient oxygen for complete oxidation of the glucose to carbon dioxide. (ii) When lactic acid accumulates in the caecum and colon it is absorbed and contributes to total blood lactic acid concentration. A build up of lactic acid in the blood reduces the animal's ability to perform at its full potential and causes pain in the muscles. A secondary effect of blood lactic acid is to reduce appetite and thereby decrease feed intake. Reduced appetite can be an important factor in situations where horses are in training and have extremely high requirements for energy in order to maintain body condition and support extended periods of exercise. Control of lactic acid production during fermentation of carbohydrate in the caecum and colon would reduce the total concentration of lactic acid in the blood and thereby contribute to a reduction in the secondary effects of this metabolite on the animal.

There have been a number of studies on development and control of lactic acidosis in sheep and cattle given excessive quantities of readily fermentable carbohydrate. The main lactate-producing bacteria are Streptococcus bovis and Lactobacillus spp. These are Gram+ve organisms and it has been shown that the build up of lactic acid may be controlled through the use of a range of antibiotic compounds specifically active against the Gram+ve bacteria. Nagaraja et al. (1981) reported that lactic acidosis could be controlled in cattle by using the ionophore compounds lasalocid or monensin. Muir et al (1980) demonstrated the control of wheat-induced acidosis in sheep using thiopeptin and related antibiotics, and Aitchison et al. (1986) found avoparcin to be particularly effective in controlling lactic acid in sheep dosed with round wheat. In all of these studies the "end-point" of lactic acidosis control was taken to be an inhibition of lactic acid build up in the rumen fluid. Laminitis is not a major problem in ruminants and in the studies mentioned above no observations were reported on the effect of the antibiotic treatments on any signs of lameness in the animals studied.

In addition to the question of whether controlling lactic acid production in the large intestine of horses will protect against laminitis there are also uncertainties in the extrapolation of the use of specific antibiotics, effective in ruminants, to equine livestock. The ruminant is a forestomach fermentor whereas the horse's fermentation compartments are in the hind gut. In the horse all material (feed, bacteria and antibiotics) pass through enzymic digestion in the stomach and small intestine before reaching the main fermentation compartments of the caecum and the large colon. Differences between the two species may therefore be expected in relation to the toxicity of the antibiotics on the host (e.g. monenesin is highly toxic to horses), the substrate to be fermented and the composition of the microbial population carrying out the fermentation.

An object of the invention is to modify the pattern of fermentation in the caecum and colon in such a way that: (i) little or no lactic acid is produced; (ii) and the pH remains within normal limits.

A second object of the invention is to increase propionate production, relative to acetate and butyrate, during hind gut fermentation.

A series of three experiments is hereinafter described which were designed to determine; (i) whether it is possible to control lactic acid accumulation in the hind gut of horses using antibiotics selective against the Gram positive organisms; (ii) whether, by preventing lactic acid accumulation during starch fermentation, laminitis could be controlled; and (iii) whether the production of propionate, during hind gut fermentation, can be increased relative to acetate or butyrate by the action of antibiotics active against Gram+ve organisms.

MATERIALS AND METHODS

In the first experiment animals were dosed with wheat slurry with and without avoparcin. Lactic acid accumulation in the hind-gut and lameness developed irrespective of the presence of avoparcin. This effectively demonstrated that the results obtained in ruminants could not necessarily be extrapolated to events in the hind gut or large intestine of the equine animal. Based on this result, the second experiment was carried out to screen a range of antibiotics for their effectiveness in controlling lactic acid production in digesta taken from the caecum and large colon of horses. This experimental programme identified virginiamycin as a compound which achieved consistent and effective control of lactic acid build up. The third experiment was conducted to investigate the effectiveness of virginiamycin in controlling lactic acid and laminitis in horses given controlled doses of ground wheat.

Experiment 1. Avoparcin in vivo

Four horses were dosed with 15 g wheat/kg liveweight. The wheat given to two of the animals contained 120 mg avoparcin/kg wheat, and the other two animals received the wheat without medication. Animals were examined prior to dosing and at intervals of eight hours after the dosing for a period of 24 hours. At these times temperature and heart rate were measured, and a sample of venous blood was taken for the measurement of pH, blood gases, bicarbonate, D-lactate and L-lactate. Animals were also examined for any signs of lameness according to the criteria of Obel (1948) as summarized by Garner et al (1977). After 24 hours all animals were slaughtered and samples of digesta were taken from the caecum and large colon for analysis of lactic acid, VFA and avoparcin concentration.

Experiment 2. In vitro screening of antibiotics for control of lactic acid accumulation Digesta was taken from the caecum and large colon from recently slaughtered animals and was filtered through nylon gauze (approximately 60 micron apertures). The fluid was diluted 1:1 with a buffer solution described by Bales et al. (1976) and incubated with wheat "corn starch" (with or without antibiotics) at 37° for 16 to 20 hours. Aliquots of digesta diluted with buffer (50 ml) were added to 100 ml conical flasks. The flasks were flushed with carbon dioxide before being sealed with a tightly fitting rubber cap. A 21 gauge needle was inserted through the rubber seal in order to allow gas to escape during the fermentation. On removal from the incubator sub-samples were immediately taken to measure L-lactic acid concentration and pH. For each treatment or level of antibiotic three replicate incubation flasks were used.

Part 1. Level of cornstarch initial testing of avoparcin, virginiamycin and flavomycin.

A range of concentrations of cornstarch providing: 0, 5, 10, 15 and 20 mg/ml diluted digesta (i.e. from 0 to 1 g cornstarch/conical flask) were tested to determine the amount required to produce a pattern of fermentation with high levels of lactic acid. Flasks were also prepared with cornstarch mixed with antibiotic premixes to provide 15 mg cornstarch/ml incubation mixture and 0, 2, 4, 8, 16 and 32 ug of avoparcin, virginiamycin or flavomycin per ml incubation mixture. After approximately 16 hour incubation at 37° samples were taken to measure lactic acid, VFA and pH.

Part 2. Effect of the antibiotics virginiamycin, flavomycin, and zinc bacitracin at concentrations below 2 ug/ml.

Incubation flasks were set up as described above with cornstarch (0.75 g) containing virginiamycin, flavomycin or zinc-bacitracin a levels to provide: 0, 0.25, 0.5, 1.0 and 2 ug antibiotic/ml incubation mixture. These flasks were incubated for 16 hours. Flasks were also set up with 0.75 g cornstarch and no antibiotic equipped with a tap and sampling tube in order to take samples from the incubation vessels at various times during the fermentation. Samples were taken at the start of the incubation and at 2, 4, 6, 8, 12 and 24 h. These were analysed for L-lactate concentration and pH.

Part 3. Further screening of avoparcin, virginiamycin, flavomycin in addition to zinc bacitracin using digesta samples taken from four horses.

All four of the antibiotics, listed above, were incubated as previously described to provide 2 ug antibiotic and 15 mg cornstarch per ml incubation mixture. There was one flask per test and each antibiotic was incubated in digesta from both the caecum and the large colon taken from each of 4 animals. Samples of incubation fluid were taken following a 20 hour incubation and were analysed for L-lactate and pH.

Part 4. Digesta samples from animals fed a pelleted diet with or without virginiamycin-metabolites pre- and post-incubation.

A total of ten horses were used for this experiment. Five horses were offered 5 kg of a pelleted mixture (ground wheat 92.5%, ground lucerne chaff 5% and 'Stafac 20' 2.5% to supply approximately 2.5 g virginiamycin. A further 5 horses were offered the same feed but without virginiamycin. Samples of caecal and large colon digesta were taken for analysis of pH, VFA, virginiamycin and L-lactate. Samples were also prepared as described above with buffer solution and incubated (1 flask/sample) with cornstarch (15 mg/ml diluted digesta). Following 20 hours incubation samples were taken for analysis of L-lactate and pH.

Part 5. Efficacy of Tylosin relative to virginiamycin

An in vitro fermentation experiment was conducted to determine the efficacy of tylosin relative to virginiamycin. Samples of strained caecal and large colon digesta (16 ml) were incubated with glucose solution (60 ug/ml) (4 ml) and varying concentrations of either tylosin or virginiamycin representing 0, 0.5, 0.1, 2.0, 4.0 ug of tylosin or virginiamycin per ml. The 25 ml containers were incubated at 37° for 20 hours. There were three replicates per treatment.

Part 6. Therapeutic use of Virginiamycin

An in vitro experiment was conducted to determine whether by adding the virginiamycin after the start of fermentation of caecal digesta and glucose subsequent lactic acid production could still be prevented.

Samples of caecal/large colon digesta were prepared as described above (Part 5) but with the following treatments (3 replicates/treatment):
(a) Control—incubated for 24 h;
(b) Sampled after 4 h and virginiamycin added before incubating for a total of 24 h;
(c) As for (b) but with sampling etc at 8 h; and
(d) As for (b) but sampling etc after 12 h. Virginiamycin was added to provide 10 ug/ml.

Experiment 3. In vivo investigation of the action of virginiamycin

Part 1. Preliminary investigation with 2 horses

These animals were pre-dosed with virginiamycin by feeding 2 kg of a mixture containing: chaff 1225 g, sugar 225 g, water 450 g and 'Stafac 20' 100 g. This provided approximately 2 g virginiamycin/d. The sugar was first dissolved in water before adding the 'Stafac 20' and mixing it into a uniform suspension. This mixture was then added to the chaff and mixed for 20 minutes. When this feed was not eaten on the second day on which it was offered the animals were dosed with 125 g 'Stafac 20'/head (2.5 g virginiamycin/head), via a stomach tube. On the third day of the experiment the animals were given a dose of ground wheat. This provided approximately 6 mg virginiamycin/kg liveweight. The wheat was mixed in a slurry with water and given in two equal amounts with an interval of about 2 hours between doses. The animals were examined and sampled at 8 hour intervals over a period of 48 hours as described for Experiment 1 above. Times were taken from the first dose of wheat.

Part 2. Main Experiment

Eight horses were used for this experiment. Four animals received virginiamycin and 4 animals received the same treatment but without virginiamycin. The animals which received virginiamycin were pre-dosed for two days prior to administration of the wheat slurry by feeding 640 g of a mixture containing lucerne chaff 495 g, sugar 16.5 g, cornflour 8.3 g, water 115 g, 'Stafac 500' 4.95 g. This provided approximately 2.48 g virginiamycin/d. This was prepared in the following way. An evenly mixed slurry of the sugar, cornflour, water and 'Stafac 500' was prepared and this was added to the lucerne chaff before mixing thoroughly in a cement mixer. The control animals received 640 g of lucerne chaff without any additive. The doses of wheat administered on the third day provided 12 grams of ground wheat/kg liveweight. Again this was given in two equal amounts with an interval between doses. The wheat given to the horses on the virginiamycin treatment contained 'Stafac 20' (20/kg wheat). This provided approximately 4.8 mg virginiamycin/kg liveweight. The animals were examined and sampled at 8 hour intervals over a period of 48 hours as described above for Experiment 1. After 48 hours all animals were slaughtered and samples of digesta were taken from the caecum and large colon for analysis of L- and D-lactic acid and pH.

RESULTS

Experiment 1

Three out of the four animals used in this experiment showed signs of Obel grade 2 lameness within 24 hours of dosing with the ground wheat. The one horse which did not show signs of lameness has lower concentrations of D-lactate than the others and at 24 hours the stomach was still full of wheat. The three animals showing signs of lameness all had high levels of D-lactate in the blood and in the large intestine digesta (see Table 1). The data in Table 1 indicate that both D- and L-lactate were present in approximately equal proportions in both caecal and large colon digesta.

FIG. 1 summarises the changes in both the blood D- and L-lactate with time after dosing with the ground wheat. The concentrations of D-lactate reached a peak at 16 hours and then decreased while L-lactate concentration was still increasing at 24 hours.

Figure 2:
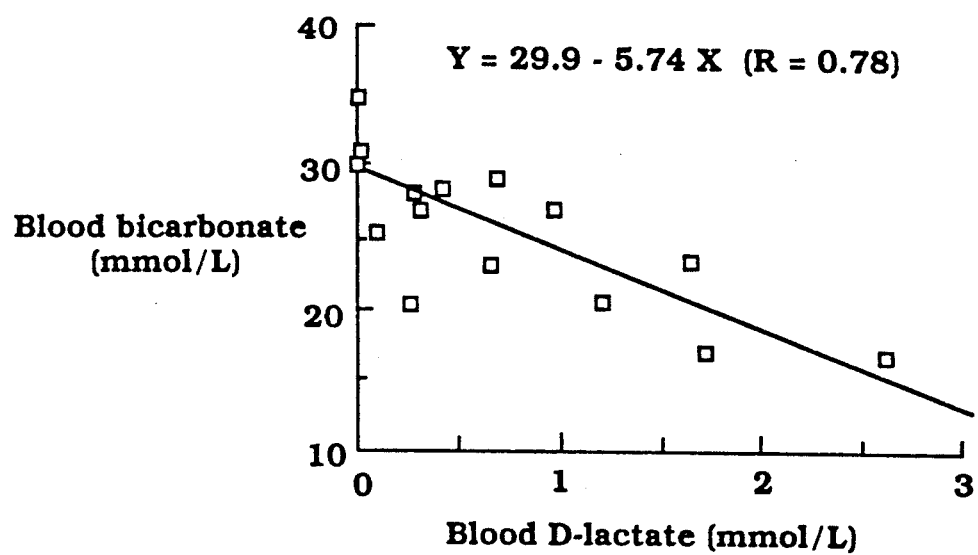

FIG. 2 shows the relationship between the concentration of blood D-lactate and the concentration of bicarbonate. While the correlation coefficient ($R^2$) for this relationship was 0.61 the equivalent value for the relationship between blood L-lactate and bicarbonate concentrations was only $R^2=0.25$.

The body temperature increased from around 37.8 (mean, all animals) at the start of the experiment to an average of 40.0 after 24 hours. The heart rate increased from approximately a mean of 44 beats/min, before dosing to an average of 60 at 16 and 24 hours.

Experiment 2

Part 1. Level of cornstarch initial testing of avoparcin, virginiamycin and flavomycin.

The effect of different amounts of cornstarch on the pH, L-lactate and VFA of incubation mixture is summarized in Table 2. There was a dose-related decrease in pH with increasing amounts of cornstarch and appreciable concentrations of L-lactate were measured in flasks containing over 10 mg cornstarch/ml incubation mixture. The addition of cornstarch increased VFA concentrations up to a maximum at 10 mg cornstarch.

The effects of antibiotics on the in vitro fermentation of buffered large intestine digesta with 15 mg cornstarch/ml are summarized in Table 3. Avoparcin only partially controlled lactic acid build-up even at 32 g/ml, virginiamycin and flavomycin gave total control at concentrations as low as 2 g/ml. Associated with the control of lactic acid by these antibiotics there was also a marked increase in pH. In the case of all of the Gram-positive antibiotics tested in this experiment there was a significant increase in the ratio of acetate:propionate.

Part 2. Effect of the antibiotics virginiamycin, flavomycin, and Zn-bacitracin at concentrations below 2 ug/ml.

The effects of the three antibiotics on L-lactate and pH are summarized in Table 4. All antibiotics significantly reduced the concentration of lactic acid and increased pH at all levels of inclusion. Virginiamycin gave the best control of lactic acid at concentrations of 1 ug/ml (virginiamycin).

The change in the concentration of lactic acid and pH are summarized in Table 5. There was little or any build-up of lactic acid until approximately 8 hours after the start of incubation with the cornstarch and no significant increase between 16 and 24 hours.

Part 3. Further screening of avoparcin, virginiamycin, flavomycin in addition to zinc bacitracin using digesta samples taken from four horses.

Table 6. summarises the mean concentrations of L-lactate and the pH of the incubation fluid following 20 hours of incubation. There was significant variation between animals in the amount of lactate produced and the presence of starch ranging from 21.3 to 21.4 to 68.5 mmol/l. Of the 5 antibiotics tested in this experiment only virginiamycin gave a significant reduction in L-lactate concentration and a significant increase in the pH of the incubation fluid. There were no significant differences in the response in the pattern of fermentation of antibiotics between the digesta taken from the caecum and the large colon and the results from both incubations have been combined. The L-lactate concentration in the fermentation fluid and the pH were closely related ($R^2=0.84$) and differences between horses and due to difference antibiotics were similar for both parameters. There were significant differences ($p<0.001$) between horses in the amount of lactate present following incubation of the digesta with cornstarch. There were also significant differences ($p<0.001$) due to the type of antibiotic used in terms of the amount of lactate accumulating and the pH of the incubation fluid. Considering the results from all horses, virginiamycin was the only antibiotic to reduce the concentration of lactate ($p<0.001$) and increase pH (p,0.01) relative to the unmedicated control incubations and relative to the other antibiotics tested. There was an indication that some of the other antibiotics had an effect on lactate production and pH in some animals.

Part 4. Incubation of digesta samples from animals predosed with virginiamycin.

Table 7 summarises the results of measurements made on blood, 'fresh digesta' and incubated samples of digesta taken from 'control' animals, and those which had been offered feed containing virginiamycin. The animals which received virginiamycin had a lower total concentration of VFA ($p<0.001$), reduced molar percentages of acetate, butyrate, isovalerate and valerate, and more than twice the molar percentage of propionate. There was no significant effect on pH of the digesta in the caecum or large colon but there was a higher ($p<0.05$) concentration of L-lactate in the caecal and large colon digesta of animals given virginiamycin.

Following incubation with cornstarch, the digesta from animals that had consumed virginiamycin produced significantly less ($p<0.001$) lactic acid than the controls. This difference was also reflected in a higher pH in the incubated digesta of animals which had received virginiamycin there was significantly less lactate produced from the incubation of the large colon digesta than was produced from the fermentation of the caecal digesta.

Part 5. Efficacy of Tylosin relative to Virginiamycin

The results presented in Table 8 indicate that tylosin can reduce the concentration of lactic acid during the fermentation of soluble carbohydrate but higher levels of tylosin than virginiamycin are required to achieve similar reduction in lacid acid levels. At the concentrations of antibiotic used in this study tylosin did not cause the same reduction in lacid acid levels as virginiamycin.

Part 6. Therapeutic use of Virginiamycin

Figure 6:
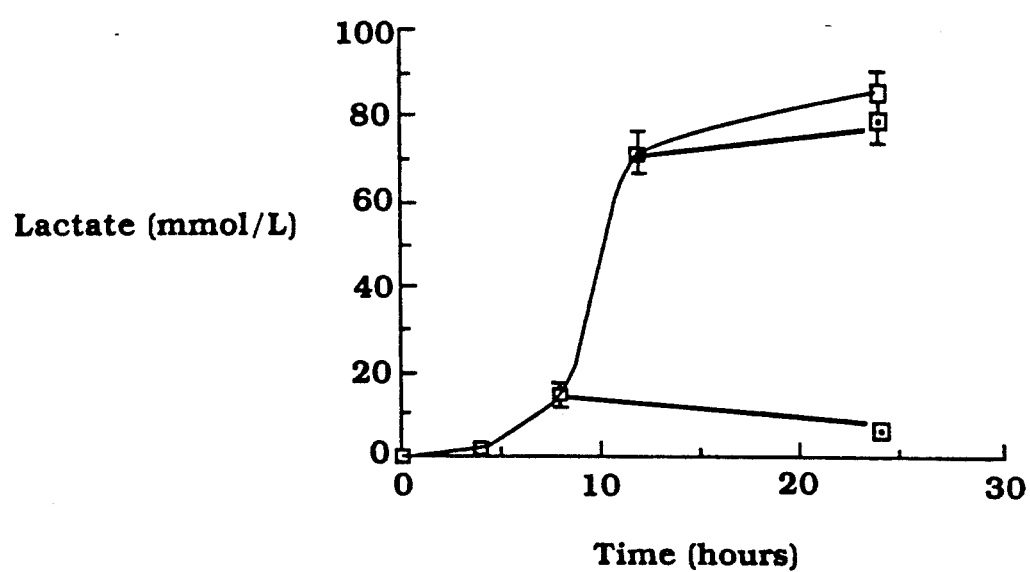

The results presented in FIG. 6 indicate that virginiamycin may be administered even after animals have consumed large quantities of grain and still prevent lactic acid build up and laminitis. It is clear that up to 8 h after the start of glucose fermentation the addition of virginiamycin prevents the build up of lactic acid. In animals fed starch-based grains the starch would first need to hydrolysed to glucose. This would allow a further delay for the therapeutic use of virginiamycin to prevent lactic acid build up.

Experiment 3. In vivo investigation of the action of virginiamycin.

Part 1. Preliminary investigation with 2 horses.

Of the two animals that received the wheat slurry with virginiamycin one died after 16 hours. The cause of death was diagnosed following post mortem examination as being a result of a build up of gas in the caecum. The second animal showed no ill effects of the dose and the results from this animal have been combined with those of the remaining 8 animals. Therefore, in the data presented there are 5 horses in the virginiamycin treatment group and 4 in the control group.

Part 2. Main Experiment

Of the 5 animals which were dosed with virginiamycin none showed any signs of lameness. In contrast, three out of the four control animals, which received no virginiamycin, developed Obel grade 2 lameness. There was therefore a significant ($p<0.05$) reduction in lameness associated with the use of virginiamycin prior to and in conjunction with the wheat slurry.

Figure 3A:
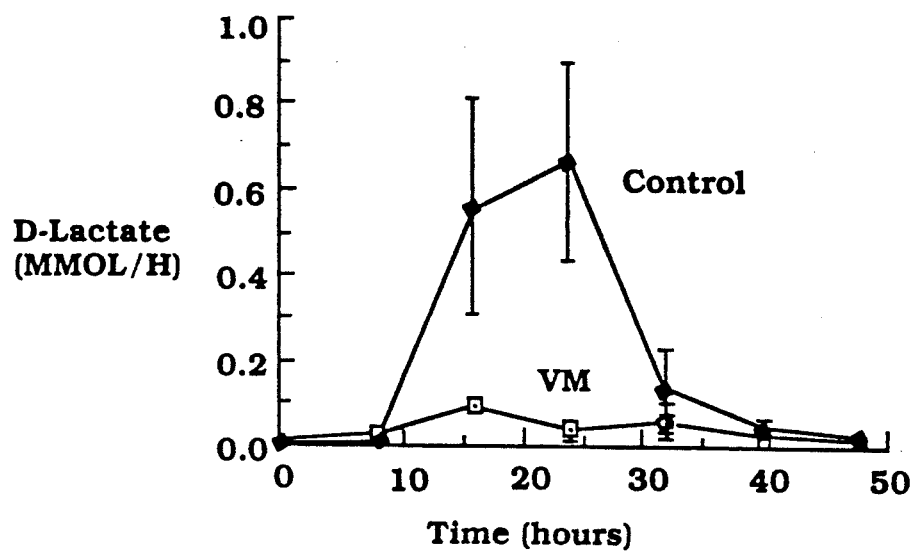
Figure 3B:
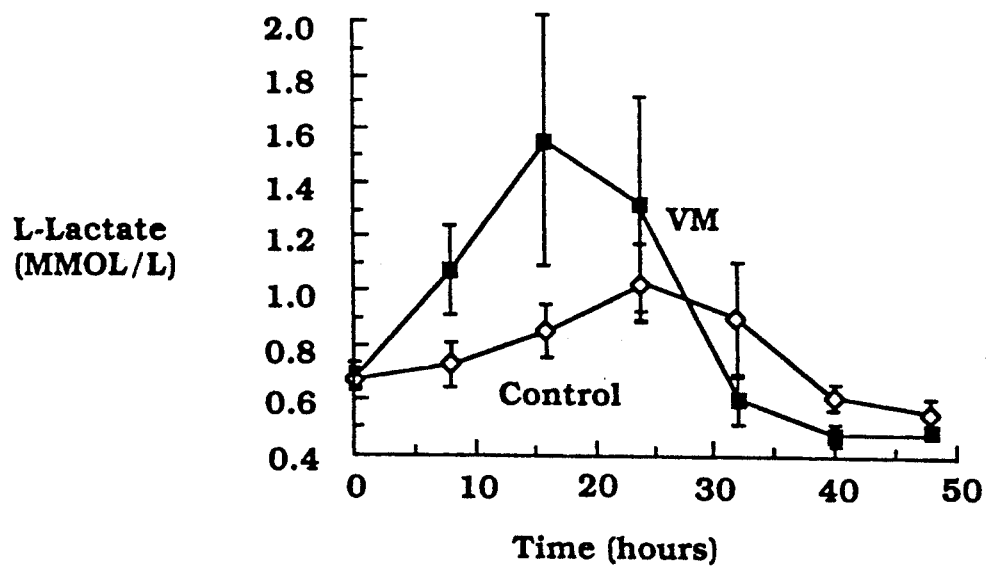

FIGS. 3(a) and 3(b) show respectively the change with time in L- and D-lactate measured in blood. There was a significant increase in D-lactate at 16 and 24 hours in the control animals whereas there was only a minor increase in the D-lactate concentrations fed virginiamycin at 16 hours. With respect to the L-lactate there was a significantly higher L-lactate concentration at 8 and 16 hours in the virginiamycin-treated animals. This trend was reversed after 24 hours and by 40 hours the L-lactate concentration was higher ($p<0.05$) in the control animals.

Figure 4A:
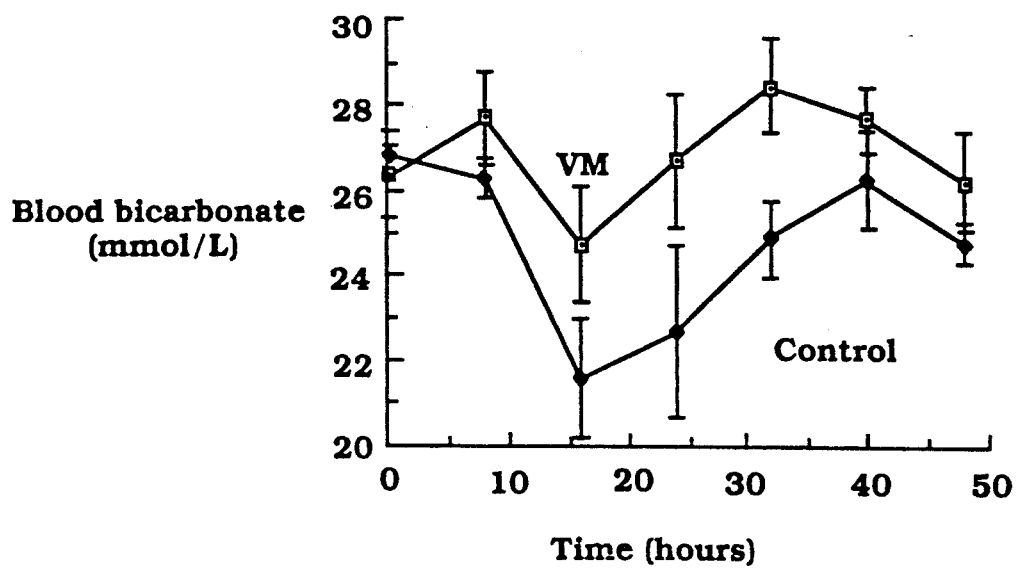
Figure 4B:
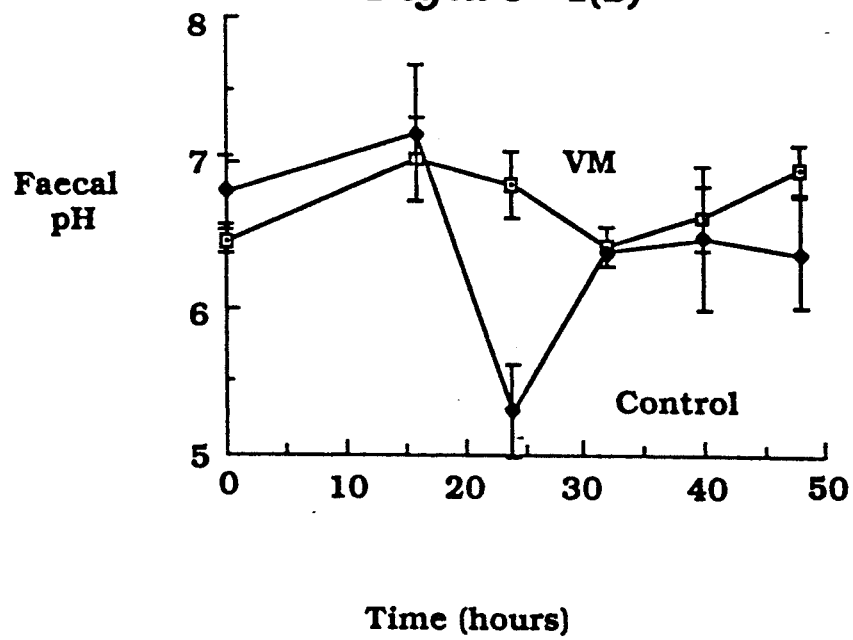

FIGS. 4(a) and 4(b) show respectively the change in blood bicarbonate and faecal pH with time after administration of the wheat slurry. There was a significant reduction in blood bicarbonate concentration in the control animals by 16 hours after dosing with wheat and levels were still lower than in the animals treated with virginiamycin at 32 hours. A similar pattern of change with time was observed in blood pH. With respect to faecal pH there was a sharp drop ($p<0.01$) in the pH of the control animals after 24 hours which returned to normal by 32 hours. There was no significant change in the faecal pH of the animals fed virginiamycin.

There was a significant relationship ($p<0.001$) between blood pH and blood D-lactate. However, there was no relationship between L-lactate and blood pH.

Figure 5:
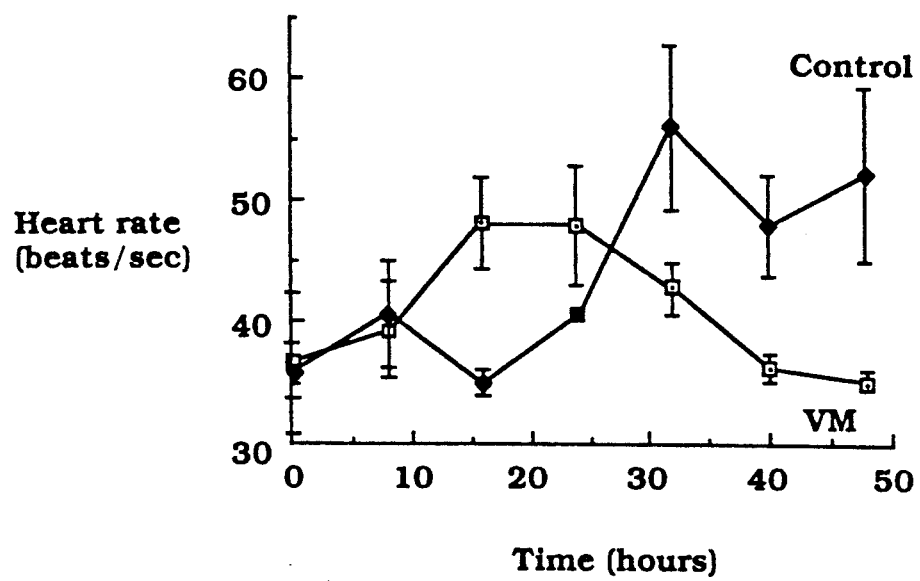

FIG. 5 shows the change in heart rate with time after administration of the wheat slurry. In the animals treated with virginiamycin, heart rate was higher than that of the control horses between 16 and 24 hours after which it returned to normal. The mean heart rate of the control animals was significantly elevated in observations taken between 24 and 48 hours.

DISCUSSION

The major finding of this series of experiments was that the administration of virginiamycin protected horses against the development of laminitis following excessive carbohydrate 'intake'. The results indicate that virginiamycin treatment maintained blood D-lactate at a low level and also controlled all parameters associated with acidosis (blood bicarbonate and pH, and faecal pH) within normal limits.

It is clear from the results of Experiment 1 that it is not possible to extrapolate from data in sheep where avoparcin was used to control lactic acidosis (Aitchison et al. 1986) to the use of avoparcin in horses for the same purpose.

It is interesting that although all of the antibiotics selected for screening in Experiment 2 have a very similar antibiotic spectrum, being active against Gram+ve bacteria, that their biological activity in controlling lactic acid build-up during the fermentation of starch was so different. It is unlikely that differences in the potency and dose rate of these antibiotics were responsible since in Expt. 2 Part 1 a very wide dose range of all compounds was used and avoparcin failed to completely control lactic acid, even at the highest concentrations (approx 32 times that of the minimum effective dose of virginiamycin).

It is also clear that there is a significant amount of variation between horses both in the amount of lactic acid produced during the fermentation of cornstarch and in the response in fermentation to different antibiotics. This variation between horses probably explains why not all horses dosed with ground wheat develop high concentrations of lactic acid in the large intestine and why they don't show signs of laminitis.

The results of in vitro fermentations were different to those measured in vivo particularly with respect to pH. In vitro, the pH of the incubation fluid was reduced irrespective of whether virginiamycin was present although virginiamycin reduced the severity of the fall in pH. On the other hand, animals treated with virginiamycin showed no depression of faecal pH or any evidence of a change in blood pH or blood biocarbonate levels. This is probably because in vivo the VFA are rapidly absorbed from the gastrointestinal tract and would not contribute to the acidity of the digesta. On the other hand lactate is not efficiently absorbed until the pH of the digesta drops to about 5.5 (Dunlop, 1965). In addition it appears (Expt. 2, part 4) that virginiamycin reduces the total concentration of VFA in vivo. This would also contribute to the higher pH of the digesta in these animals.

The results of Expt. 1 show that in the animals receiving avoparcin (horses 2 and 4) the concentrations of the antibiotic were lower in the caecum than in the large colon. Lactic acid concentrations were appreciably lower in the large colon digesta of animals given avoparcin than in the caecal contents of the same animals. It therefore appears that the fine antibiotic particles do not remain in the caecum long enough to have a significant effect on the pattern of fermentation in that compartment. This is an important point in that it indicates a need for development of a formulation work to get the antibiotic to the caecum. This formulation would need to be of a particulate and/or fibrous nature to enhance its movement into the caecum. It is believed that the particle size may need to be at least or the order of 1 mm.

It is clear (Tables 2 and 7) that virginiamycin and other Gram+ve antibiotics increase the molar proportion of propionate during hind gut fermentation. It is possible that increased propionate production could increase the availability of substrate for glucose syntheses and therefore glycogen deposition.

It appears that in animals treated with virginiamycin more gas was produced during the initial rapid fermentation of the carbohydrate. This was seen in the animal that died from the build up of gas in the caecum and also from the rise in L-lactate in the period from 16 to 24 hours (FIG. 3). The reason for this build up of gas is probably due to the fact that VFA and not lactate continue to be produced during fermentation of the starch in the virginiamycin-treated horses. When the VFA, acetate and butyrate are produced carbon dioxide and hydrogen are also produced. These can also combine to produce methane. No such production of gas accompanies the formation of lactate or propionate. It should be stressed that the carbohydrate overload model used here provides extreme quantities of readily fermentable carbohydrate over a very short period and it is possible that under more physiological conditions this build-up of gas would not occur. Virginiamycin actually increases the amount of propionate produced relative to acetate and butyrate (Table 7) and under normal conditions of a VFA-based fermentation would be expected to reduce the amount of gas produced.

The fact that lactate concentrations do not continue to build up once virginiamycin is introduced into the digesta contents, indicates that it may be possible to administer virginiamycin after animals have accidently consumed large quantities of high-starch carbohydrate and in this way prevent lactic acid accumulation and laminitis. From the data presented in FIG. 3 it appears that D-Lactate only rises significantly approximately 16h after dosing with wheat. It seems reasonable to expect that treatment with virginiamycin up to 12h after accidental ingestian of high levels of starch would prevent laminitis.

TABLE 1

Concentrations of D- and L-lactic acid isomers and avoparcin in the caecum and large colon of three horses 24 hours after administration of ground wheat (15 g/kg liveweight). Also shown is whether or not the animals showed signs of lameness

| | horse number: | | | |
|---|---|---|---|---|
| Avoparcin in feed (mg/kg wheat) | 1 0 | 3 0 | 2 120 | 4 120 |
| Caecum | | | | |
| L-lactic acid (mmol/L) | 0.04 | 32 | 33 | 37 |
| D-lactic acid (mmol/L) | 0.0 | 35 | 33 | 34 |
| avoparcin (μg/g digesta) | 0 | 0 | 17 | 15 |
| Large colon | | | | |
| L-lactic acid (mmol/L) | 1.4 | 27 | 2 | 10 |
| D-lactic acid (mmol/L) | 1.0 | 34 | 2 | 11 |
| avoparcin (μg/g digesta) | 0 | 0 | 30 | 25 |
| Lameness | none | Obel 2 | Obel 2 | Obel 2 |

TABLE 2

Results of an in vitro fermentation experiment in which equine caecal/large colon digesta was incubated with different concentrations of cornstarch.

| Level of Cornstarch (mg/ml) | pH Mean | pH SE | Lactate Mean | Lactate SE | Total VFA Mean | Total VFA SE | Acet:Prop Mean | Acet:Prop SE |
|---|---|---|---|---|---|---|---|---|
| 0 | 6.95 | 0.013 | 0.1 | 0.03 | 63.7 | 1.89 | 9.4 | 0.39 |
| 5 | 6.53 | 0.001 | 0.0 | 0.00 | 93.7 | 2.20 | 3.9 | 0.14 |
| 10 | 5.89 | 0.142 | 15.1 | 6.72 | 121.1 | 2.16 | 2.7 | 0.06 |
| 15 | 5.34 | 0.042 | 46.8 | 2.93 | 97.5 | 6.56 | 2.9 | 0.18 |
| 20 | 5.23 | 0.035 | 56.2 | 1.39 | 93.4 | 1.93 | 3.3 | 0.03 |

TABLE 3

Effect of the antibiotics avoparcin, virginiamycin and flavomycin on pH, L-lactate and VFA during the incubation of mixed caecal/large colon digesta with buffer and cornstarch (15 mg/ml).

| Antibiotic (μg/ml) | pH Mean | pH SE | Lactate Mean | Lactate SE | Total VFA Mean | Total VFA SE | Acet:Prop Mean | Acet:Prop SE |
|---|---|---|---|---|---|---|---|---|
| Avoparcin | | | | | | | | |
| 0 | 5.34 | 0.042 | 46.8 | 2.93 | 97.5 | 6.56 | 2.9 | 0.18 |
| 2 | 6.14 | 0.054 | 8.9 | 1.04 | 102.6 | 1.92 | 2.9 | 0.05 |
| 4 | 6.17 | 0.017 | 12.0 | 2.41 | 100.9 | 2.12 | 2.8 | 0.06 |
| 8 | 6.33 | 0.006 | 11.0 | 0.42 | 82.1 | 4.92 | 3.3 | 0.06 |
| 16 | 6.40 | 0.017 | 10.3 | 1.40 | 87.1 | 2.49 | 3.5 | 0.15 |
| 32 | 6.43 | 0.012 | 15.1 | 0.57 | 89.8 | 2.33 | 3.6 | 0.16 |
| Virginiamycin | | | | | | | | |
| 0 | 5.34 | 0.042 | 46.8 | 2.93 | 97.5 | 6.56 | 2.9 | 0.18 |
| 2 | 6.57 | 0.009 | 0.2 | 0.05 | 93.2 | 5.15 | 2.9 | 0.10 |
| 4 | 6.63 | 0.003 | 0.2 | 0.07 | 80.8 | 8.99 | 3.1 | 0.07 |
| 8 | 6.66 | 0.009 | 0.2 | 0.10 | 79.7 | 8.75 | 3.2 | 0.03 |
| 16 | 6.64 | 0.010 | 0.0 | 0.01 | 71.3 | 10.59 | 3.8 | 0.23 |
| 32 | 6.66 | 0.09 | 0.1 | 0.04 | 87.1 | 0.74 | 3.7 | 0.08 |
| Flavomycin | | | | | | | | |
| 0 | 5.34 | 0.042 | 46.8 | 2.93 | 97.5 | 6.56 | 2.9 | 0.18 |
| 2 | 6.57 | 0.006 | 0.0 | 0.01 | 88.9 | 5.07 | 3.4 | 0.01 |
| 4 | 6.52 | 0.009 | 0.0 | 0.01 | 93.7 | 2.71 | 4.6 | 0.16 |
| 8 | 6.48 | 0.033 | 0.0 | 0.01 | 90.0 | 3.46 | 5.7 | 0.10 |
| 16 | 6.47 | 0.030 | 0.0 | 0.02 | 85.6 | 10.11 | 5.8 | 0.30 |
| 32 | 6.41 | 0.023 | 0.2 | 0.06 | 93.7 | 11.98 | 5.8 | 0.18 |

TABLE 4

The effect of virginiamycin, flavomycin, ardacin, and Zn-bacitracin on L-lactate and pH when caecal/large colon digesta was incubated with buffer and cornstarch.

| Antibiotic conc'n (μg/ml) | Virginiamycin Mean | Virginiamycin SE | Flavomycin Mean | Flavomycin SE | Zn-bacitracin Mean | Zn-bacitracin SE |
|---|---|---|---|---|---|---|
| | L-lactate (mmol/L) | | | | | |
| 0.00 | 66.5 | 11.07 | 66.5 | 11.07 | 66.5 | 11.07 |
| 0.25 | 28.4 | 1.16 | 12.4 | 2.36 | 20.6 | 0.82 |
| 0.50 | 28.8 | 3.16 | 7.3 | 1.75 | 17.8 | 1.93 |
| 1.00 | 3.2 | 1.82 | 9.9 | 0.97 | 15.9 | 1.42 |
| 2.00 | 1.4 | 0.18 | 11.7 | 0.32 | 14.7 | 1.85 |
| | pH | | | | | |
| 0.00 | 5.23 | 0.090 | 5.23 | 0.090 | 5.23 | 0.090 |
| 0.25 | 5.45 | 0.022 | 5.69 | 0.096 | 5.64 | 0.044 |
| 0.50 | 5.44 | 0.024 | 5.67 | 0.081 | 5.86 | 0.033 |
| 1.00 | 5.66 | 0.048 | 5.67 | 0.057 | 5.68 | 0.010 |
| 2.00 | 5.78 | 0.208 | 5.56 | 0.051 | 5.59 | 0.033 |

TABLE 5

The change in L-lactate concentration with time during the incubation of equine caecal fluid with cornstarch and a buffer solution. Three incubation vessels were samples at each time.

| Incubation time (h) | L-lactate (mmol/L) Mean | s.e. | pH |
|---|---|---|---|
| 0 | 1.6 | 0.00 | 7.3 |
| 2 | 1.5 | 0.03 | 7.3 |
| 4 | 1.0 | 0.23 | 7.2 |
| 6 | 1.2 | 0.26 | 7.1 |
| 8 | 9.5 | 4.07 | 7.0 |

TABLE 5-continued

The change in L-lactate concentration with time during the incubation of equine caecal fluid with cornstarch and a buffer solution. Three incubation vessels were samples at each time.

| Incubation time (h) | L-lactate (mmol/L) Mean | s.e. | pH |
|---|---|---|---|
| 12 | 47.7 | 8.12 | 6.2 |
| 16 | 66.5 | 11.07 | 5.4 |
| 24 | 75.7 | 8.51 | 5.2 |

TABLE 6

The effect of avoparcin (Avop), virginiamycin (VM), flavomycin (Flavo), ardacin and zinc bacitracin (ZnBac), on the fermentation of caecal and large colon contents with buffer solution and cornstarch on L-lactate and pH. Values shown are the means of separate incubations of digesta samples from the caecum and large colon.

| Horse | Control | Avop | VM | Flavo | ZnBac |
|---|---|---|---|---|---|
| | | L-lactate | | | |
| 1 | 30.3 | 19.8 | 0.3 | 31.8 | 26.8 |
| 2 | 68.5 | 67.9 | 34.1 | 55.6 | 62.5 |
| 3 | 32.5 | 34.5 | 7.6 | 17.9 | 35.1 |
| 4 | 21.4 | 20.0 | 12.3 | 23.7 | 22.2 |
| Mean | 38.2 | 35.5 | 13.6 | 32.2 | 36.6 |
| SE | 7.35 | 8.01 | 5.15 | 5.86 | 6.38 |
| | | pH | | | |
| 1 | 4.88 | 5.12 | 5.40 | 4.88 | 4.91 |
| 2 | 4.61 | 4.57 | 4.94 | 4.54 | 4.59 |
| 3 | 4.79 | 4.75 | 5.17 | 4.98 | 4.76 |
| 4 | 5.12 | 5.15 | 5.27 | 5.07 | 5.11 |
| Mean | 4.85 | 4.90 | 5.19 | 4.86 | 4.84 |
| SE | 0.075 | 0.101 | 0.069 | 0.081 | 0.079 |

TABLE 7

The concentration of metabolitics (mmol/L) measured in "fresh digesta" and incubated digesta from the caecum and large colon of animals which had received no virginiamycin (control) and those which had received a feed containing virginiamycin approximately 14 hours before slaughter. (n = 5 animals in each mean)

| | Control | | | | Virginiamycin | | | |
|---|---|---|---|---|---|---|---|---|
| | Caecum | | Colon | | Caecum | | Colon | |
| Metabolite | Mean | se | Mean | se | Mean | se | Mean | se |
| Blood D-lactate | | | | | | | | |
| "Fresh digesta" | | | | | | | | |
| pH | 6.3 | 0.11 | 6.3 | 0.18 | 6.2 | 0.20 | 6.0 | 0.32 |
| L-lactate | 0.8 | 0.29 | 7.5 | 2.35 | 10.3 | 3.91 | 10.2 | 4.10 |
| Total VFA | 143.2 | 12.56 | 199.3 | 12.12 | 76.1 | 13.34 | 118.7 | 9.47 |
| % Acetate | 68.7 | 1.26 | 68.1 | 2.11 | 50.3 | 4.33 | 52.1 | 4.11 |
| % Propionate | 22.9 | 1.61 | 22.0 | 2.55 | 46.5 | 4.75 | 44.3 | 4.50 |
| % Butyrate | 8.4 | 0.75 | 9.9 | 1.00 | 3.2 | 1.24 | 3.6 | 0.87 |
| % Iso-valerate | 0.9 | 0.23 | 3.8 | 0.83 | 0.0 | 0.00 | 1.5 | 0.64 |
| % Valerate | 0.0 | 0.00 | 1.9 | 0.58 | 0.5 | 0.41 | 0.2 | 0.21 |
| Incubated digesta | | | | | | | | |
| pH | 4.8 | 0.10 | 4.9 | 0.10 | 5.2 | 0.08 | 5.3 | 0.14 |
| L-lactate | 38.1 | 7.19 | 42.0 | 12.01 | 5.5 | 2.64 | 1.8 | 1.31 |

TABLE 8

The efficacy of tylosin relative to virginiamycin when caecal/large colon digesta was incubated with glucose.

| Antibiotic Concentration (μg/ml) | Virginiamycin | | Tylosin | |
|---|---|---|---|---|
| | L-Lactate (mmol/L) | | | |
| | Mean | SE | Mean | SE |
| 0.00 | 111 | 2.0 | 114 | 2.0 |
| 0.50 | 25. | 2.2 | 122 | 2.0 |
| 1.00 | 9.3 | 2.3 | 45.1 | 2.2 |
| 2.00 | 11.0 | 2.3 | 38.7 | 2.2 |
| 4.00 | 7.7 | 2.3 | 11.7 | 2.3 |

I claim:

1. A method of treating laminitis in equine livestock which comprises dosing said equine with a pharmaceutically effective quantity of an agent comprising virginiamycin, virginiamycin M or virginiamycin S wherein said agent acts to treat laminitis in the equine livestock.

2. A method as claimed in claim 1 wherein said method is for treating equine livestock which are subjected to a high carbohydrate diet by controlling lactic acid concentration in the hind gut of the animal.

3. A method as claimed in claim 2 wherein said agent is administered regularly throughout the period the animal is subjected to a high carbohydrate diet.

4. A method as claimed in claim 2 wherein said agent is administered in a single dose subsequent to the animal's consumption of an excessive quantity of high carbohydrate food stuff.

5. A method as claimed in claim 1 wherein said agent comprises virginiamycin.

6. A method as claimed in claim 1 wherein said agent comprises virginiamycin S.

7. A method as claimed in claim 1 wherein said agent comprises virginiamycin M.

8. A method as claimed in claim 1 wherein the virginiamycin comprises a mixture of virginiamycin S and virginiamycin M.

9. A method as claimed in claim 1 wherein the virginiamycin or virginiamycin S or virginiamycin M is administered in a particulate form able to withstand enzymatic digestion in the upper alimentary canal of the animal.

10. A method as claimed in claim 1 wherein uptake of the virginiamycin or virginiamycin S or virginiamycin M in the caecum is enhanced by administering the agent in a particulate form.

11. A method as claimed in claim 1, wherein the virginiamycin or virginiamycin S or virginiamycin M is administered in the form of particles of at least 1 mm in size.

12. A method as claimed in claim 1 wherein the virginiamycin or virginiamycin S or virginiamycin M is administered in the form of particles which are fibrous.

13. A method as claimed in claim 1 wherein the virginiamycin or virginiamycin S or virginiamycin M is administered orally.

14. A method of treating laminitis as recited in claim 1, wherein said agent acts to treat laminitis by controlling lactic acid concentration in the hind gut.

15. A method of treating laminitis as recited in claim 1, wherein said agent acts to improve the efficiency of feed utilization in the equine livestock by increasing the production of proprionate during fermentative digestion in the hind gut and allows feeding to the equine livestock diets containing high levels of a readily fermentable carbohydrate.

* * * * *